United States Patent [19]
Howarth

[11] 3,994,602
[45] Nov. 30, 1976

[54] OPTICAL REFLECTANCE GAUGE AND METHOD THEREFOR

[75] Inventor: John J. Howarth, San Jose, Calif.

[73] Assignee: Measurex Corporation, Cupertino, Calif.

[22] Filed: May 12, 1975

[21] Appl. No.: 576,543

Related U.S. Application Data

[63] Continuation-in-part of Ser. No. 433,269, Jan. 14, 1974, abandoned.

[52] U.S. Cl. ............................. 356/208; 356/103; 356/210
[51] Int. Cl.² ........................................ G01N 21/26
[58] Field of Search ........... 356/103, 104, 201, 204, 356/206, 207, 208, 209, 210, 212

[56] References Cited
UNITED STATES PATENTS

| | | | |
|---|---|---|---|
| 3,586,862 | 6/1971 | Topol | 356/208 |
| 3,659,943 | 5/1972 | Goolsby | 356/209 |
| 3,714,444 | 1/1973 | Carr et al. | 356/208 |
| 3,819,278 | 6/1974 | Muller | 356/208 |
| 3,861,802 | 1/1975 | Belmear | 356/103 |
| 3,867,033 | 2/1975 | Hasinger | 356/103 |
| 3,870,417 | 3/1975 | Bashark | 356/209 |

Primary Examiner—John K. Corbin
Assistant Examiner—Richard A. Rosenberger
Attorney, Agent, or Firm—Flehr, Hohbach, Test Albritton

[57] ABSTRACT

An optical reflectance gauge which serves as a chlorination sensor for paper pulp in which a spectrum of the bulk of the material is obtained by use of displaced windows in the pulp pipe. One window has a radiation source associated with it and the other a radiation detector. The distance between such windows is determined to provide for insensitivity to small changes in consistency for measurement of chlorination. A mechanical arrangement is also provided for easier coupling of the gauge to a pulp pipe.

14 Claims, 13 Drawing Figures

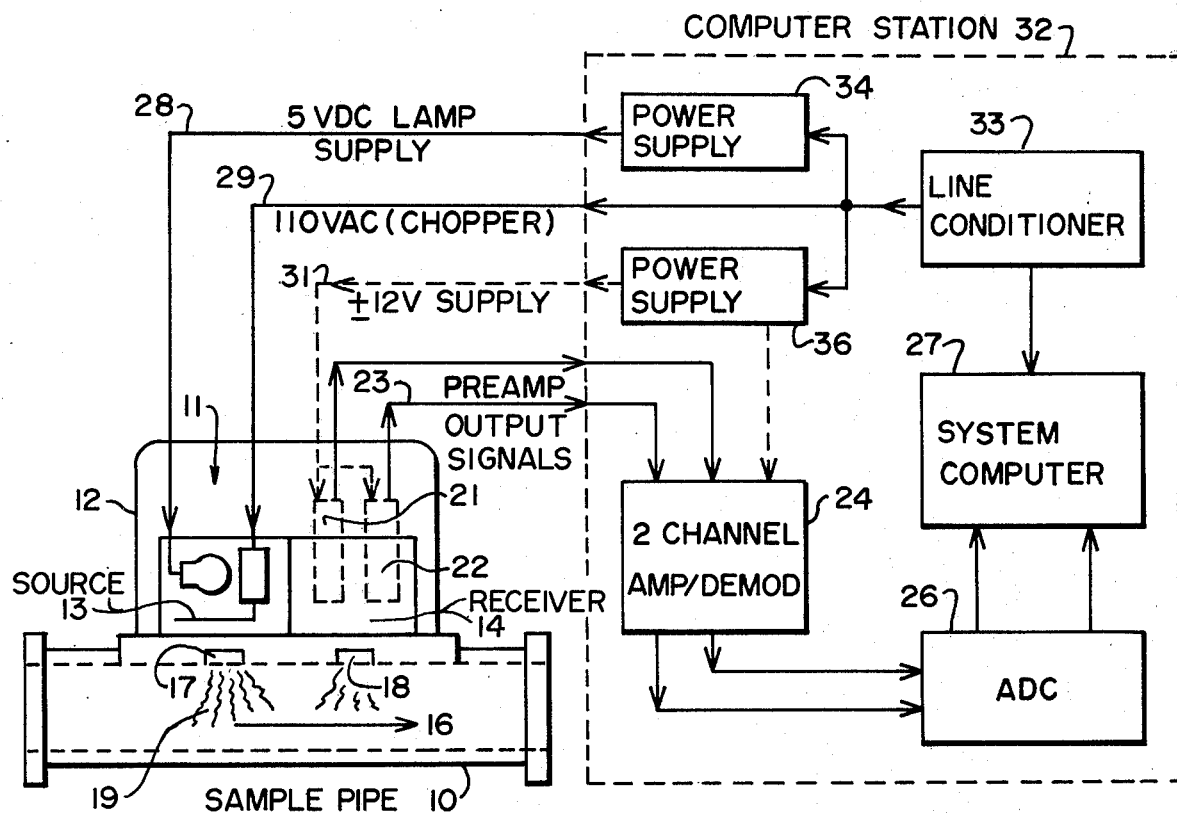
FIG. 1
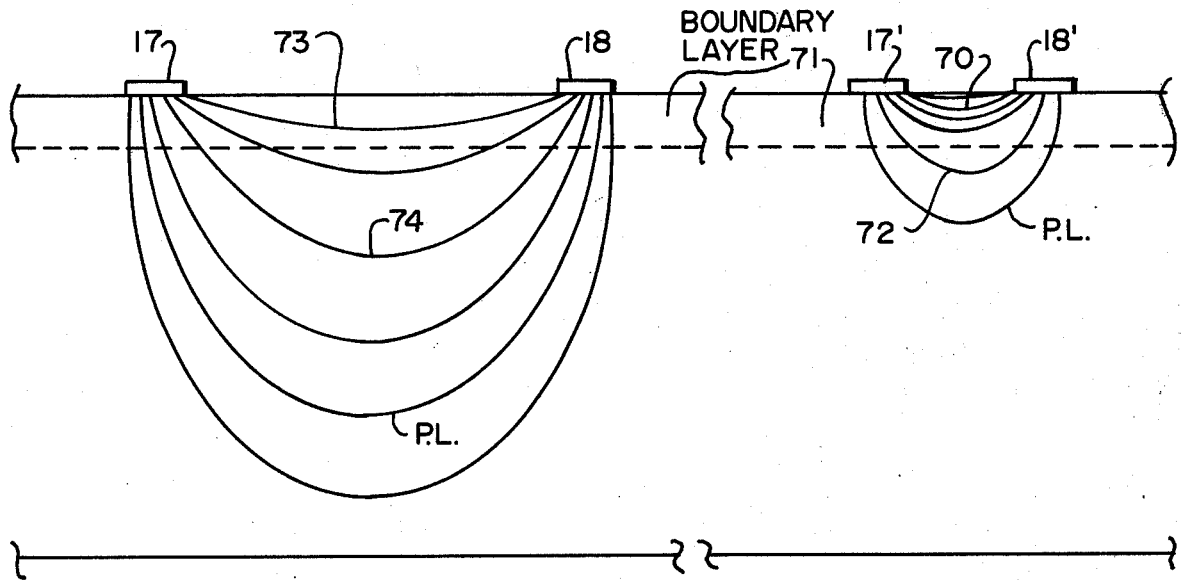
FIG. 2B
FIG. 2A

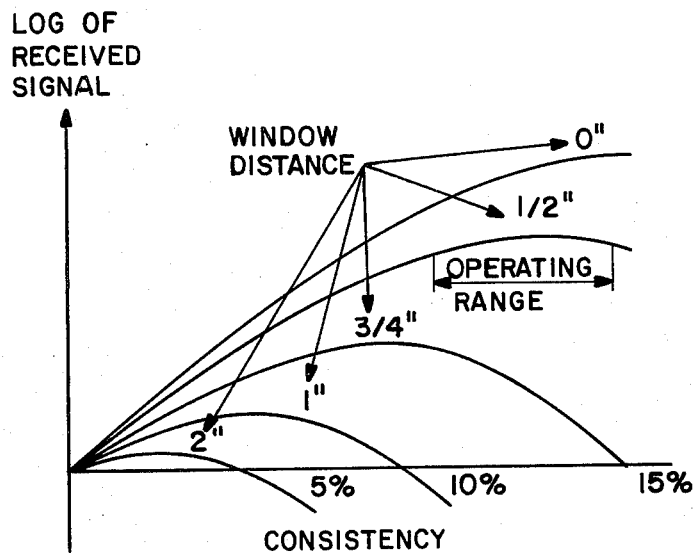
FIG.—9
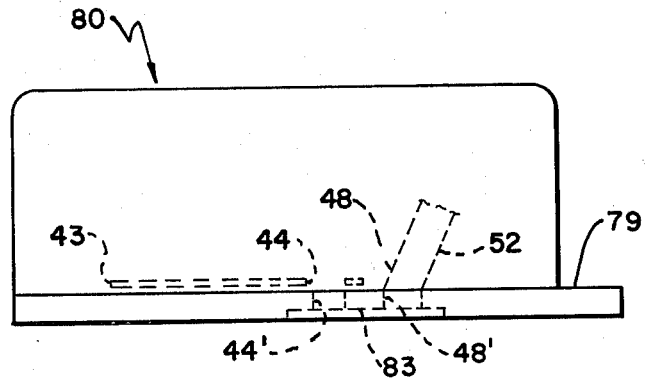
FIG.—10A
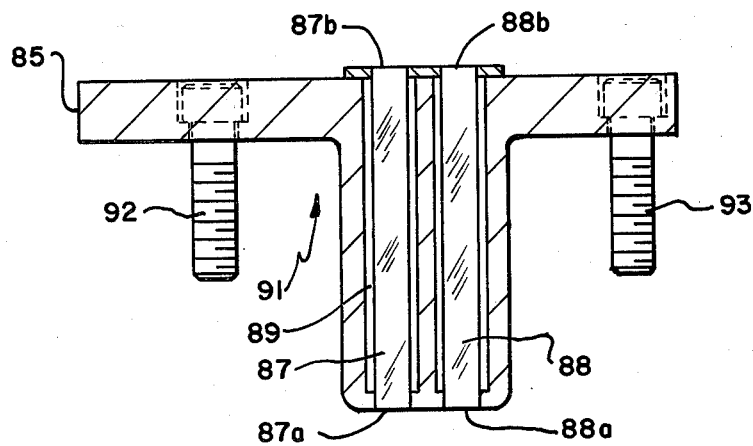
FIG.—10B
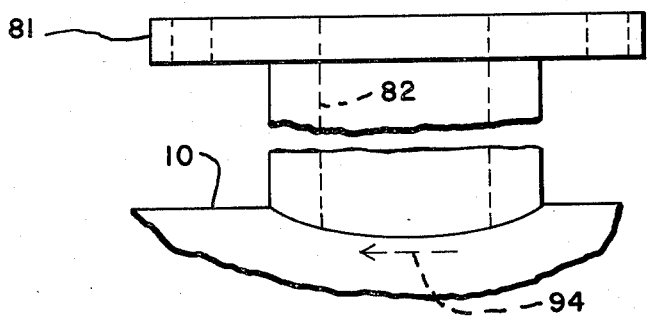
FIG.—10C

OPTICAL REFLECTANCE GAUGE AND METHOD THEREFOR

CROSS-REFERENCE TO RELATED APPLICATION

This application is a continuation-in-part of application Ser. No. 433,269, filed Jan. 14, 1974, entitled "Optical Reflectance Gauge and Method Therefor" in the name of John J. Howarth and assigned to the present assignee and now abandoned.

BACKGROUND OF THE INVENTION

The present invention is directed to an optical reflectance gauge and method therefor and more specifically a gauge for measuring pulp optical properties.

Control of the chlorination stage of a bleaching plant is normally based on Kappa Number. That is, the chlorination stage is normally controlled to hold the amount of lignin residing on the pulp fibers (after chlorination and caustic extraction) constant. For such measurements, a standard transmission type gauge although desirable cannot be used because the pipe diameters necessary to pass this viscose material make the optical path so long that the signals are completely attenuated. This invention is essentially a single side transmission measurement in which the optical path is determined by the window separation.

Optical reflectance gauges have been developed in which a single window in the pulp pipe is used. Here a wide spectrum light source illuminates the passing pulp and one or more detectors provide electrical signals indicative of reflectance. These sensors, however, are limited by sensitivity to pulp consistency variation, pitch buildup, and boundary layer effects. Specifically, near the window a layer of stagnant material, such as black liquor, may occur. Also dirt or pitch may accumulate on the inside of the window to cause an erroneous color indication. In the case of simple reflection most of the returning optical signal is from the layer adjacent to the window.

The consistency of pulp has heretofore either been indirectly measured or directly measured by a mechanical impeller which is large and expensive. It has been discovered that consistency is related to pulp optical properties.

OBJECTS AND SUMMARY OF THE INVENTION

It is, therefore, a general object of the present invention to provide an improved optical reflectance gauge and method therefor.

It is another object of the invention to provide a gauge as above which has low consistency cross-sensitivity on pulp measurements.

It is another object of the invention to provide a gauge as above which is less sensitive to fouling of the window through which measurements are being made and also to boundary layer effects.

It is another object of the invention to provide improved apparatus as above for coupling the gauge to a pulp pipe.

In accordance with the above objects there is provided an optical reflectance gauge for measuring the bulk reflectance of a flowing liquid material. A source of radiation is provided. First window means couple the source to the flowing material. Radiation detector means are provided for receiving radiation from said source. Second window means couple the detector means to the material with the second window means being displaced from the first window means a sufficient distance to cause substantially all of the received radiation to be transmitted through the bulk portion of the material.

BRIEF DESCRIPTION OF THE DRAWINGS

FIG. 1 is a block diagram embodying the present invention;

FIGS. 2A and 2B are optical diagrams useful in understanding the invention;

FIG. 9 is similar to FIG. 6 but on a larger scale; and

FIGS. 10A, B and C is an exploded view of an alternative embodiment of the invention.

DETAILED DESCRIPTION OF THE PREFERRED EMBODIMENT

Figure 3:
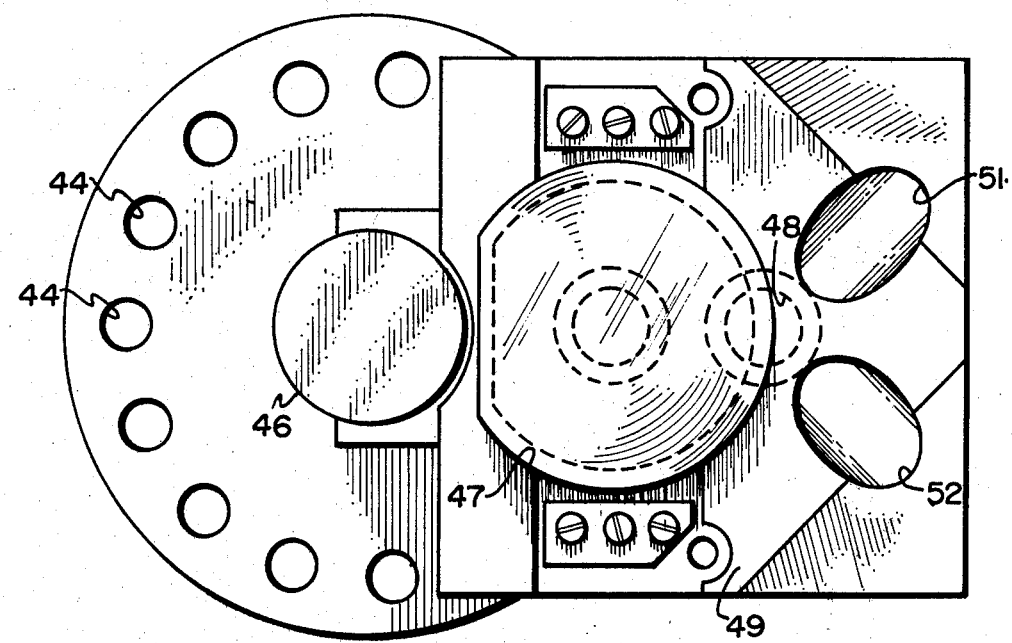
FIG. 3 is an elevational view partially in section of a portion of FIG. 1 which illustrates one embodiment of the present invention.

The present invention in one embodiment finds preferred usage as a chlorination sensor at the chlorination tower or premixer of the bleach portion of a paper making plant. The use of such chlorination sensor in a plant as above is fully disclosed and claimed in a copending application in the names of Brewster and Robinson, entitled "Bleach Plant Control Method," Ser. No. 246,628 filed Apr. 24, 1972, and assigned to the present assignee and now abandoned. In the above application, the sensor is illustrated as being located on a pipeline carrying paper pulp between two portions of the bleach plant.

Such pipe 10 is illustrated in FIG. 1 which has mounted on it a chlorination sensor 11 in a sealed enclosure 12. The sensor 12 includes a source portion 13 and a receiver portion 14. In general, source 13 provides a wide spectrum of radiation which is coupled to the material 16 flowing in pipe 10 through a window 17. Radiation detector or receiver 14 is also coupled to material 16 through a window 18 which is displaced in distance from window 17 as will be discussed in detail below. The windows 17 and 18 are preferably of translucent quartz to provide in the case of transmission window 17 full diffusion of the source radiation into material 16 as shown at 19 and in the case of receive window 18 a solid half angle of received radiation which is detected by a sample radiation detector 21 and a reference radiation detector 22. This use of diffusing windows futher reduces the effect of pulp noise (short term variations in consistency due to its flocculent nature).

In general, when the radiation 19 enters the pulp 16 it permeates the pulp medium and diffuses randomly in all directions to be thus strongly affected by the bulk properties. In addition, window 18 is located far enough from window 17 so that only radiation which has been transmitted through the desired path lengths of the bulk material is received. This is in contrast to radiation which is merely reflected from the surface of the material flowing close to window 17. In other words, the transmission of radiation 19 through the material gives a bulk rather than a surface effect; i.e., this interaction of radiation with the bulk of the material is, for purposes of this invention, called bulk reflectance.

FIG. 2A illustrates the effect of improper spacing of windows 17' and 18' where the path lengths (P.L.) vary substantially. The actual optical paths in the pulp are random. However, as shown in FIGS. 2A and 2B they are illustrated as typical mean paths. When the windows are close together, as illustrated in FIG. 2A, a typical optical path 70 of photons going through the boundary layer 71 is substantially shorter than the shortest path 72 that goes through the bulk material. As a result, the intensity of light from path 70 will dominate that of path 72. In contrast, when the windows are spaced further apart as illustrated in FIG. 2B, the optical path 73 of photons going through the boundary layer is nearly the same length as the shortest path 74 that goes through the bulk material. Since there are substantially more optical paths in the bulk material the radiation received from these paths will predominate in the FIG. 2 situation. In other words, FIG. 2A is a demagnified version of FIG. 2B but the boundary layer 71 remains the same size. Thus in FIG. 2B with proper window spacing most of the photon paths lie outside of the boundary layer.

The signals from radiation detectors 21 and 22 are coupled on the lines 23 to a two channel amplifier demodulator 24. In a manner well known in the paper making art in conjunction with moisture measurement, the sample and the reference signals are ratioed, converted to a digital value in analog to digital converter 26 and coupled to the system computer 27 for further use as for example, in a system as described in the above copending Brewster et al. application. The reference wavelength received by detector 22 has a wavelength of 0.8 micron or greater and the sampled wavelength received by detector 21 encompasses the range 0.4 to 0.7 microns. The reference wavelength is only slightly affected by the change of reflectance of the material due to chlorination whereas the sample wavelength is highly sensitive. In contrast to competitive designs which are essentially two wavelength color meters, this technique measures the entire visible spectrum and compares it with a reference in the near IR.

Chlorination sensor 11 also has the appropriate voltage supplies which includes a 5 volt dc lamp supply on line 28 to radiation source 11, a 110 volt ac supply on line 29 which drives a chopper to provide for greater circuit stability and a 12 volt supply on line 31 for the receiver portion 14. In the computer station 32 which includes system computer 27 and the other electronis of the system, a line conditioner 33 supplies the appropriate voltages through power supplies 34 and 36.

Figure 4:
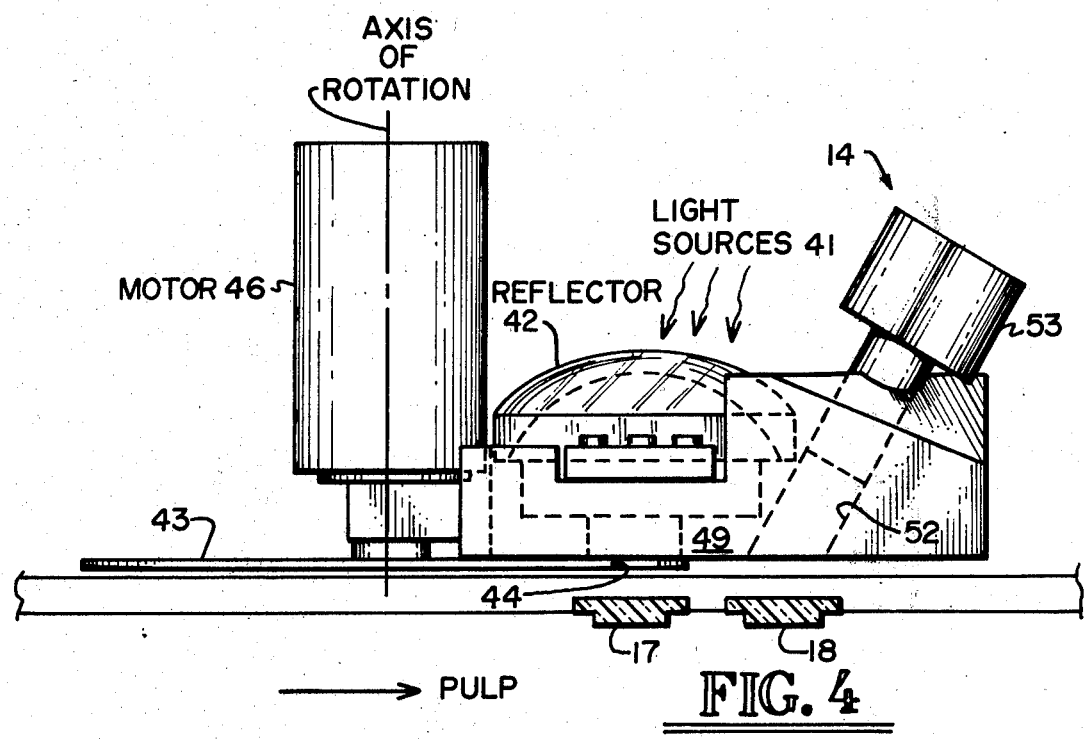
FIG. 4 is a top view of FIG. 3.

FIG. 3 illustrates the chlorination sensor 11 and the radiation source 13 and receiver 14. Source 13 includes light sources 41 which are aimed toward a dome-shaped reflector 42 to be reflected toward window 17. This light is interrupted by a chopper wheel 43 having apertures 44 cut therein and which is driven by a motor 46. Such apertures are shown in FIG. 4. Also referring to FIG. 3 as well as to FIG. 2, the light sources 41 are mounted in a circular cavity 47.

Figure 5:
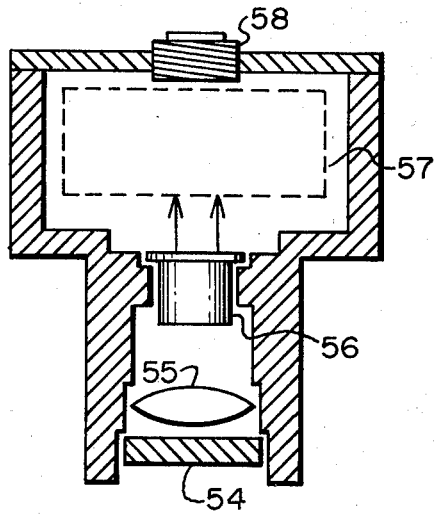
FIG. 5 is a detailed cross-sectional view of a portion of FIG. 3.

Receiver portion 14 includes two detectors; one for the reference wavelength and the other for the sample wavelength which are coupled to the common window 18 through the aperture 48 as best illustrated in FIG. 4. The channels 51 and 52 for the apertures which converge at window 18 are drilled through the block 49. A typical detector 53 is shown inserted in drill hole 52 and is also shown in cross section in FIG. 5 and includes a color filter 54 having a pass band for the appropriate sample or reference wavelength, a lens 55, radiation detector 56, preamp 57 and an electrical connector 58. As is apparent from examination of window 18 in FIG. 3, this diffusion window provides a solid half angle of reradiation so that the detectors which are angled through holes 51 and 52 are fully sensitive to such reradiation. The foregoing is disclosed and claimed in a copending application Ser. No. 475,628, filed June 3, 1974, in the name of John J. Howarth entitled "Apparatus For Measuring A Predetermined Characteristic of a Material Using Two or More Wavelengths of Radiation", and assigned to the present assignee now abandoned.

Figure 6:
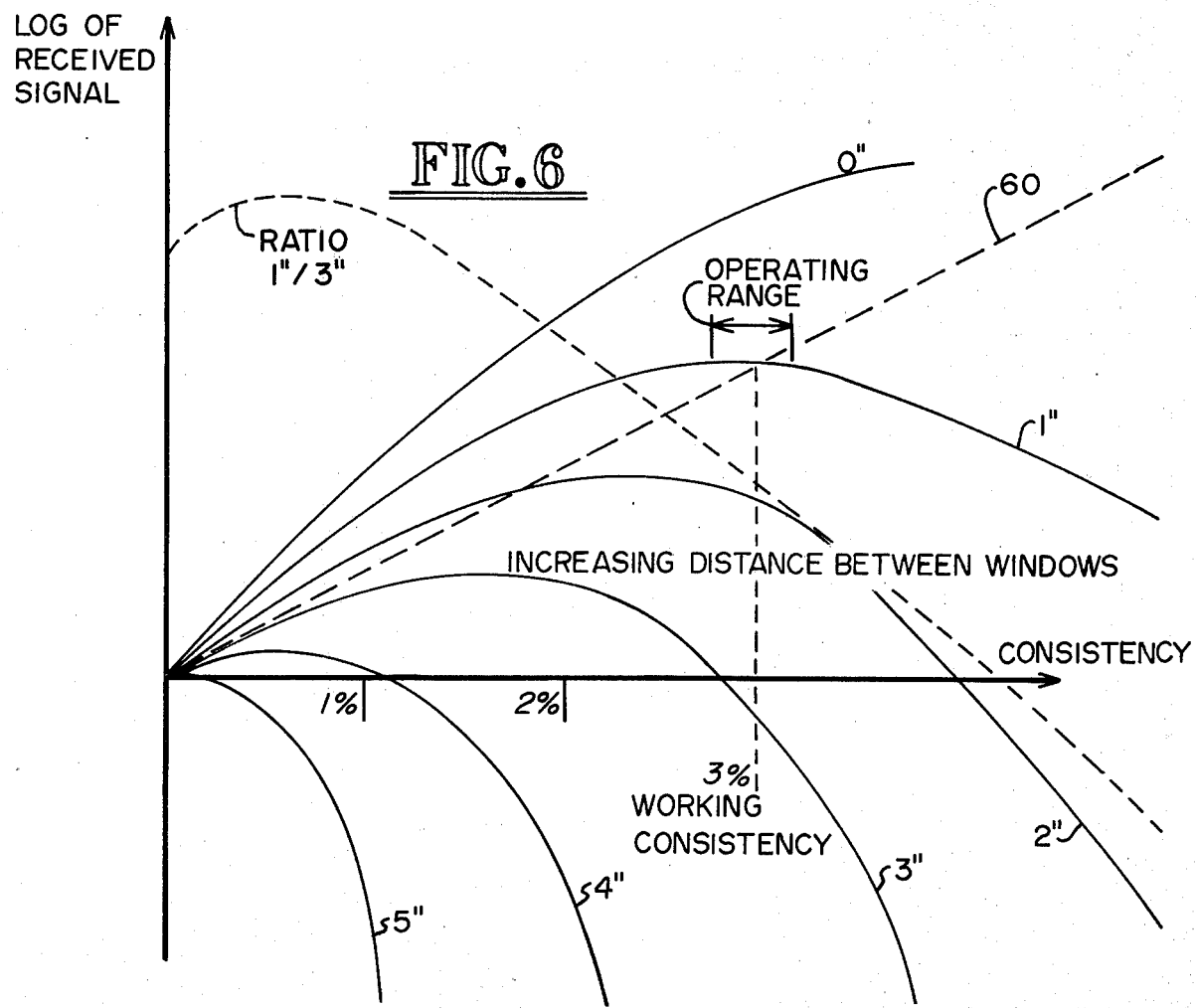
FIG. 6 are characteristic curves useful in understanding and in constructing the present invention.

FIG. 6 illustrates the relationship between consistency and the received signal at receiver 14 with distance between windows 17 and 18 as the parameter. These are, therefore, labeled with their nominal inch values of 0, 1, 2 and 3. Consistency is in percent and the working or nominal consistency of the paper pulp being measured by the system is assumed to be 3%. In choosing the optimum displacement distance between windows 17 and 18, nonlinear relationships of the curves of FIG. 6 must be constructed. After the working or nominal consistency of the system (3% in the preferred embodiment) is chosen, then the displacement distance of the windows is chosen which will give an operating range as indicated in FIG. 6 which is substantially horizontal; that is, where small changes in consistency around the working consistency cause no change in received signal. From a practical standpoint most systems have a nominal consistency of 3%. Thus an off-the-shelf gauge can be provided. This thus decouples consistency from reflectance measurements to make the received signal substantially independent of normal changes in consistency. Cross sensitivity with consistency variations is further reduceed by using a ratio of two optical signals which have simultaneously followed the same path.

It has also been discovered that the bulk optical reflectance properties of pulp material may in many circumstances provide an accurate measurement of consistency (but such measurements may not succeed if clay or titanium dioxide is present). The curves of FIG. 6 below line 60 illustrates the foregoing since the received radiation, $I$, varies in accordance with consistency by $$I = I_o e^{-\mu cl}$$

where $I_o$ is the initial calibration value, $\mu$ is a mass constant of said material, $l$ is the mean path length of said received radiation, and $C$ is the consistency of the material.

Thus, any of the sloping portions of the curves below line 60 (which obeys the above Beer's Law) are suitable for use in consistency measurement, assuming of course that the curve represents the bulk optical property as discussed above.

However, in order to reduce the effects of pitch and dirt as well as pulp noise (caused by the flocculent nature of the pulp) it is preferred to measure the ratio of received radiation in at least two different window locations as illustrated by the dashed curve labeled Ratio 1/3.

Figure 7:
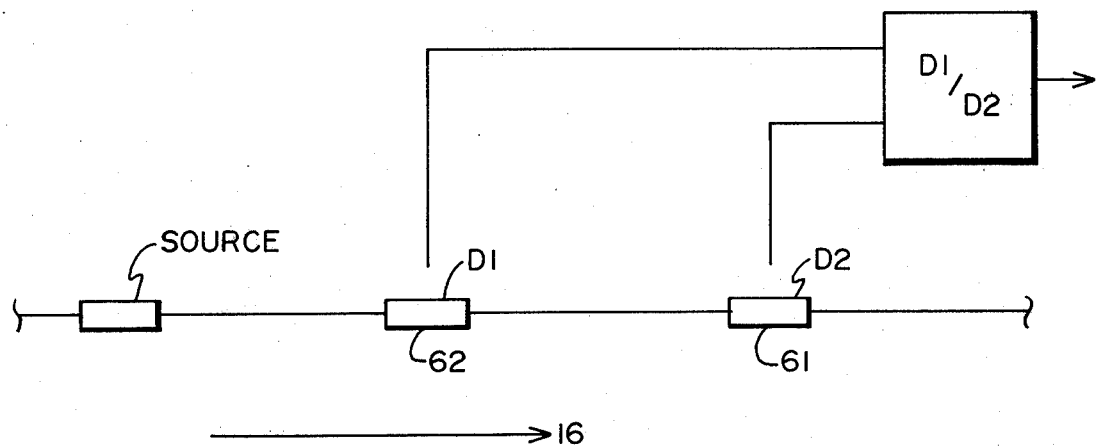
FIG. 7 is a simplified schematic of another embodiment of the invention similar to a portion of FIG. 1.
Figure 8:
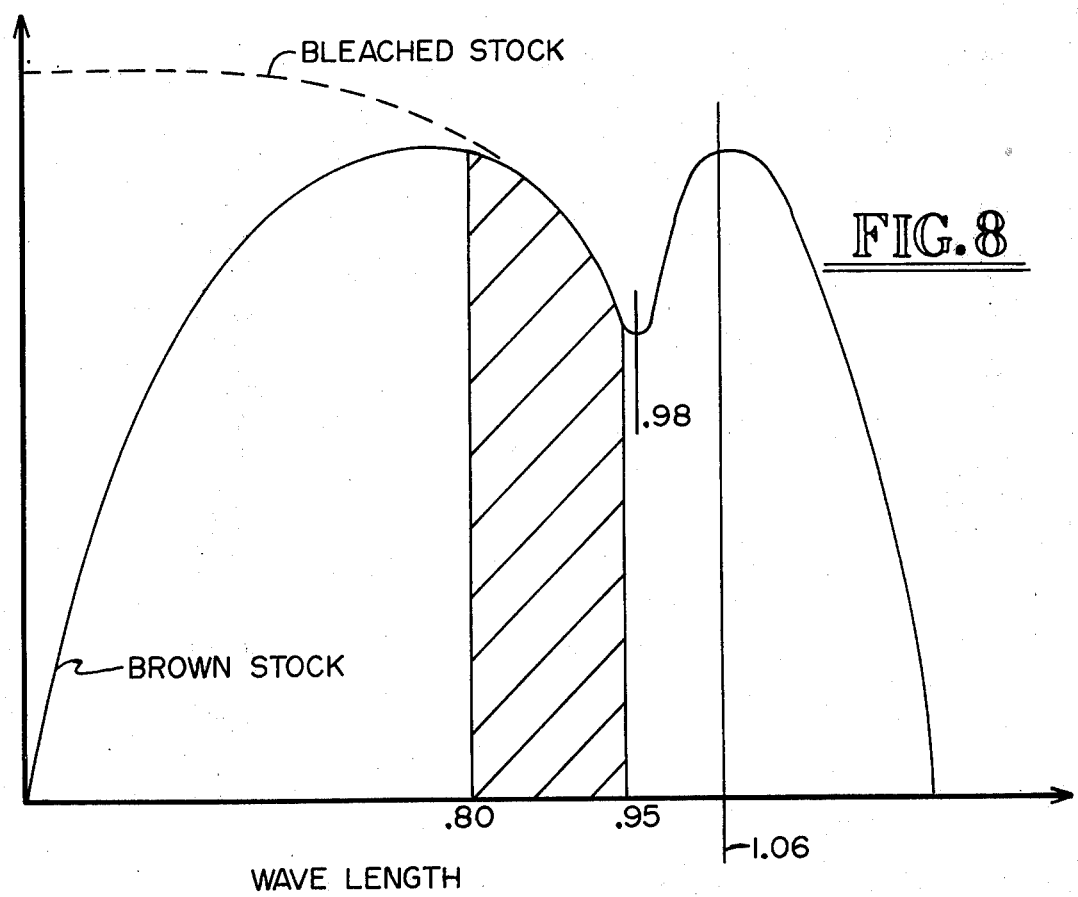
FIG. 8 are transmission curves for pulp.

In FIG. 7 a third window 61 is displaced from the source a greater distance than window 62 the placement corresponding to the 3 inch and 1 inch curves of FIG. 6. Radiation detectors D1 and D2 associated with the window receive radiation of a common wavelength which is ratioed as illustrated to produce the dashed ratio curve of FIG. 6. Such wavelength, as shown in FIG. 8 is within the range of 0.8 to 0.95 microns. Such range is effective for both bleached and brown stock.

As was discussed previously, the gauge of the present invention is preferably used or located on the pipeline carrying paper pulp between two portions of a bleach plant. In the earlier stages of such a plant, consistency as indicated in FIG. 6 is in the operating range of 3%. However, in the later stages consistency may increase to as much as 12%. This might occur, for example, at the entrance to the hypochlorite tower. Where it is desired to provide for either feedback or feedforward control of the degree of bleaching or rather the amount of lignin. The gauge of the present invention is ideally suited as a brightness sensor at this high consistency location. Although implicitly illustrated in the curves of FIG. 6, FIG. 9 shows the curves of FIG. 6 as they would be naturally extended to higher operating consistencies. Specifically in accordance with the theory discussed above, with higher operating consistencies, the distance between windows is decreased; thus typically for a nominal 12% consistency it has been found that a ½ inch window distance should be used in the context of the present invention.

It is important to recognize that even though the theory underlying the invention implicitly covers the situations from less than 3% consistency to 12% and beyond, the actual physical appearance and characteristic of the pulp is dramatically different at these extremes. At 3% consistency, the suspension is a typical liquid with a typical boundary layer and can be pumped as any other liquid. At 12% consistency, the material is a solid— you can walk on it. It has to be forced down the pipes by screws, and there are no boundary layers. Thus, the entire material may be thought of as being in bulk form. But when the mean optical path length is determined as illustrated in FIG. 9 by correctly choosing the window aperture very accurate results are obtained. Thus, the gauge of the present invention is remarkably versatile.

Referring to FIGS. 10A, 10B and 10C in many instances the mounting of the gauge of the present invention on a pipeline carrying pulp in the mechanical configuration as illustrated in FIGS. 1 and 4 may be relatively difficult. This is especially true when the pipe diameter is either relatively small or relatively large; problems also arise due to the thickness of the pipe itself. In addition, from both an original construction and repair standpoints, the configuration of FIG. 4 may present some problems.

FIGS. 10A through 10C are an exploded view of a novel mechanical arrangement for optically coupling the electronic package or unit of the gauge illustrated at 80 with the pipeline 10 illustrated in FIG. 10C. This is accomplished by providing a mounting flange 81 having a central aperture 82 which extends into the pipeline and, of course, the flowing liquid material. The electronics unit 80 consists of all electronic and mechanical portions of the gauge outside of the pipeline as illustrated in FIGS. 3 and 4 with the exception of the diffusion windows 17 and 18. Referring specifically to FIG. 10A, the components are mounted on a base plate 79 with a recessed aperture 83, exposing a radiation transmitting window 44' (which is coupled to the radiation source through the chopper wheel 43 and its apertures 44) and a radiation receiving window 48' similar to window 48 of FIG. 3. Window 48 communicates with drill holes 51 and 52 also shown in FIG. 3 the drill holes receiving at their ends the two detectors 14.

In accordance with the invention, radiation transmission means are provided for coupling the pipeline aperture 82 to the optical reflectance measuring unit 80. These means, referring to FIG. 10B, include a pair of clear quartz elongated rods 87 and 88 having first and second ends designated with the suffixes $a$ and $b$, respectively. Rods 87 and 88 are coated with an aluminized coating along their lengths to provide for efficient passage of the radiation between their ends. In addition, a coating material 89 permanently locates the rods parallel to each other and in a liquid impenetrable assembly unit 91 which, of course, includes a mating flange 85. The ends 87a and 88a are polished to prevent the buildup of dirt and the ends 87b and 88b are rough ground with 150 to 180 grit to effectively provide diffusion windows. They serve the same purpose as windows 17 and 18 as illustrated in FIG. 4 and are in the same relative location with respect to the measuring unit components due to inset 83. Mating flange 85 when affixed to mounting flange 81 by means of fasteners 92 and 93 cause the ends 87a and 88a to extend into pipeline 10 in the same manner as windows 17 and 18 as indicated in FIGS. 1 and 4.

At this point in time, a liquid proof seal is provided in the pipeline with the ends 87b and 88b being of course exposed to the ambient atmosphere. Thereafter, the measuring unit 80 and its base plate 79 may be attached on top of flange 85 by suitable fasteners. With the windows 44' and 48' juxtaposed with the ends 87b and 88b effectively the same operation is achieved as illustrated in FIGS. 1 and 4. However, ease of mounting initially and repair of the entire gauge package has been vastly improved. For example, aperture 82 need only be approximately 3 inches in diameter for the most common installations. Since pipeline 10 may be under high pressures, this minimum disturbance of the pipeline is desirable. Assembly 91 provides a waterproof fit with both the aperture 82 and the flange 81 so that the electronics unit 80 may be easily removed for repair. Such seal must normally resist the 60 foot pressure head produced by the associated chlorination tower.

Rods 87 and 88 are illustrated in the present embodiment as being cylindrical and positioned on a line along the line of flow 94 of the liquid material. However, their shape can be modified depending on the material being measured and their location varied to minimize noise in the material and to average out irregularities. For example, in very high consistency paper pulp the pulp is of a flocculent nature. Thus, the radiation transmission channels 87 and 88 could be of a rectangular configuration with the long axes of the rectangles being parallel to the liquid flow direction. Thus, in essence the unit of FIG. 10B would be rotated by 90°.

In conclusion, the present invention has provided an improved optical reflectance gauge and a method therefor which produces a strong spectrum of the bulk of the material so that the buildup of dirt on the measuring window or boundary layer effects do not cause significant errors in the readings. For purposes of chlorination sensing the consistency is decoupled. In addition to its usage in a pipeline as shown in the present embodiment, the gauge may also be used in a non-pipe environment such as the side of a chlorination tower or vessel. The arrangement of FIG. 10 provides for easy coupling of the electronic package of the gauge to a pipeline or vessel or any similar container.

What is claimed is:

1. An optical reflectance gauge for measuring the bulk reflectance of a material having a nominal consistency comprising: a source of radiation; first window means for coupling said source to said material; radiation detector means for receiving radiation from said source; second window means for coupling said detector means to said material said second window means being displaced from said first window means a sufficient distance to cause substantially all of the received radiation to be transmitted through the bulk portion of said material and also at a distance so that small changes in said consistency do not affect the amount of said received radiation.

2. A gauge as in claim 1 where said window means include diffusing material.

3. A gauge as in claim 1 where said detector means includes a reference detector of one wavelength and a sample detector of another wavelength both of said detectors being coupled to a common window means which constitutes said second window means.

4. A gauge as in claim 3 where said common window means includes diffusing means to cause reradiation through a solid half angle of received radiation from said source.

5. A gauge as in claim 1 where said received radiation is transmitted from said source along a plurality of paths most of which lie outside of a boundary layer.

6. A gauge as in claim 1 where said displacement of said windows is along the flow path of said material which is a flowing liquid.

7. A gauge as in claim 1 where said window means includes a pair of elongated radiation transmission channels.

8. A gauge as in claim 8 where said channels include first and second ends one pair of said ends being roughened to provide for diffusion of said radiation.

9. A method of measuring the bulk optical reflectance of a material having a nominal consistency comprising the following steps: directing a source of radiation at one portion of said material; positioning a radiation detector for receiving radiation transmitted through said material at another portion of said material displaced from said one portion; determining the relationships of the consistency of said material with received radiation with displacement as a parameter; fixing said displacement where the nominal consistency coincides with a portion of one of said relationships which provide substantially no change in said received radiation for small changes in consistency from said nominal value and where substantially all of the received radiation is transmitted through the bulk portion of said material.

10. An optical reflectance gauge for measuring the bulk reflectance of a material having a nominal consistency in a container comprising; mounting flange means coupled to said container and having an aperture extending into said vessel or container; an optical reflectance measuring unit including a source of radiation having a first window for transmitting radiation of said source, radiation detector means, and a second window for receiving radiation and coupling it to said radiation detector means; radiation transmission means for coupling said container aperture to said optical reflectance measuring unit including a pair of solid elongated radiation transmission channels, each having first and second ends, a liquid impenetrable assembly for retaining said elongated channels in fixed alignment with each other and having flange means for mating with said mounting flange means for providing a liquid proof seal and for locating said channels within said aperture so that said first pair of ends are exposed to said material said first pair of ends being spaced a sufficient distance to cause substantially all of the received radiation to be transmitted through the bulk portion of said material and also at a distance so that small changes in said consistency do not affect the amount of said received radiation; said measuring unit including means for connecting said first and second windows in respective juxtaposition with said second pair of ends.

11. A gauge as in claim 10 where said second pair of ends provides a diffusing surface.

12. A gauge as in claim 10 where said elongated channels are clear quartz rods coated with aluminum.

13. An optical gauge for measuring the bulk reflectance of a solid-like material having a nominal consistency comprising: a source of radiation; first window means for coupling said source to said material; radiation detector means for receiving radiation from said source; second window means for coupling said detector means to said material said second window means being displaced from said first window means a distance such that small changes in said consistency do not affect the amount of said received radiation.

14. An optical reflectance gauge for measuring the bulk reflectance of a flowing liquid material in a pipeline comprising; mounting flange means coupled to said pipeline and having a central and elongated aperture extending into said pipeline; a unitary optical reflectance measuring unit including a base plate, a source of radiation having a first window in said base plate for transmitting radiation of said source, radiation detector means, and a second window in said base plate for receiving radiation and coupling it to said radiation detector means; unitary radiation transmission means for coupling said pipeline aperture to said optical reflectance measuring unit including a pair of solid elongated radiation transmission channels, each having first and second ends, a liquid impenetrable assembly for retaining said elongated channels in fixed alignment with each other and having flange means for mating with said mounting flange means for providing a liquid proof seal and for locating said channels within said central aperture so that said first pair of ends are exposed to said flowing liquid material and said second pair of ends are substantially in the same plane as the top surface of said flange means of said assembly; means for fastening said flange means of said liquid impenetrable assembly to said mounting flange means; fastening means for attaching said base plate to the top surface of said flange means of said assembly for connecting said first and second windows in respective juxtaposition with said second pair of ends.

* * * * *